US012606560B1

(12) United States Patent
Mitchell et al.

(10) Patent No.: US 12,606,560 B1
(45) Date of Patent: *Apr. 21, 2026

(54) METHOD OF CONVERTING MITRAGYNINE TO 7-HYDROXYMITRAGYNINE

(71) Applicants: Haywood Max Mitchell, Santa Barbara, CA (US); Cecil Page, Ojai, CA (US); Joseph William Merino, Oxnard, CA (US)

(72) Inventors: Haywood Max Mitchell, Santa Barbara, CA (US); Cecil Page, Ojai, CA (US); Joseph William Merino, Oxnard, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/086,822

(22) Filed: Mar. 21, 2025

Related U.S. Application Data

(63) Continuation of application No. 18/664,689, filed on May 15, 2024, now Pat. No. 12,466,830.

(51) Int. Cl.
*C07D 471/14* (2006.01)

(52) U.S. Cl.
CPC ................................... C07D 471/14 (2013.01)

(58) Field of Classification Search
CPC ............................ C07D 471/14; A61K 31/437
USPC ............................................. 546/70; 514/285
See application file for complete search history.

(56) References Cited

U.S. PATENT DOCUMENTS

| | | | |
|---|---|---|---|
| 10,961,244 | B2 | 3/2021 | Kruegel et al. |
| 11,760,758 | B2 | 9/2023 | Kruegel et al. |
| 11,912,707 | B2 | 2/2024 | Kruegel et al. |
| 2006/0258721 | A1 | 11/2006 | Maddaford et al. |
| 2019/0255036 | A1 | 8/2019 | Kariman |
| 2023/0276830 | A1 | 9/2023 | Mirzakhanov |

FOREIGN PATENT DOCUMENTS

| | | |
|---|---|---|
| CN | 106967067 A | 7/2017 |
| WO | 2016176657 A1 | 11/2016 |
| WO | 2017165738 A1 | 9/2017 |
| WO | 2020037136 A1 | 2/2020 |

OTHER PUBLICATIONS

Amorim, Daniela, "Pharmacological Treatment of Neuropathic Pain: Review of Oral and Topical Therapy Recommendations", Clinical Neurosciences and Mental Health, Published Jul. 28, 2015, ARC Publishing.

Araujo et al., "Antinociceptive Effects of (O-methyl)-N-benzoyl Tyramine (Riparin I) from Aniba Riparia (Nees) Mez (Lauraceae) in Mice", Naunyn-Schmied Arch Pharmacol (2009) 380:337-344.

Johnson, L.E. et al., "The Potential for Kratom as an Antidepressant and Antipsychotic", Yale Journal of Biology and Medicine; 93; (2020), pp. 283-289.

Kopf, J., "Opioids and Potentiators: A Dangerous Combination", The Recovery Village. 2023; pp. 1-7 https://www.therecoveryvillage.com/opiate-addiction/opioids-potentiators/ last visited Jul. 15, 2024.

Kruegel et al., "7-Hydroxymitragynine is an Active Metabolite of Mitragynine and a Key Mediator of its Analgesic Effects", ACS Central Science, 2019, 5, pp. 992-1001, Supporting information 1-12 (Year: 2019).

Obara, I., et al. "Histamine, Histamine Receptors, and Neuropathic Pain Relief", British J. Pharmacology Society 2020; 177:580-599 (Year: 2020).

Raffa, Robert B., et al., "Central Administration of p-octopamine to Mice: Assessment of Antinociception", European Journal of Pharmacology, 169 (1987) 317-320.

The Wayback Machine, Accurate Education Vitamin C; Accurate Clinic, May 2021 https://web.archive.org/web/20210507084638/https://accurateclinic.com/accurate-education-vitamin-c/ last visited Jul. 15, 2024.

*Primary Examiner* — Charanjit Aulakh
(74) *Attorney, Agent, or Firm* — Shore IP Group, PLLC; Sean R. Wilsusen

(57) ABSTRACT

A method of converting mitragynine to 7-hydroxymitragynine includes dissolving a predetermined volume of mitragynine extract in a solvent to form a first mitragynine solution. The method includes adding a second solution including sodium bicarbonate and water and a third solution including oxone monopersulfate and water to the first vessel including the first mitragynine solution. The first mitragynine solution is allowed to react with the second solution including sodium bicarbonate and water and the third solution including oxone monopersulfate and water to form a second mitragynine solution including 7-hydroxymitragynine. The method includes separating the 7-hydroxymitragine from the second mitragynine solution and collecting a high-purity 7-hydroxymitragynine product.

13 Claims, 9 Drawing Sheets

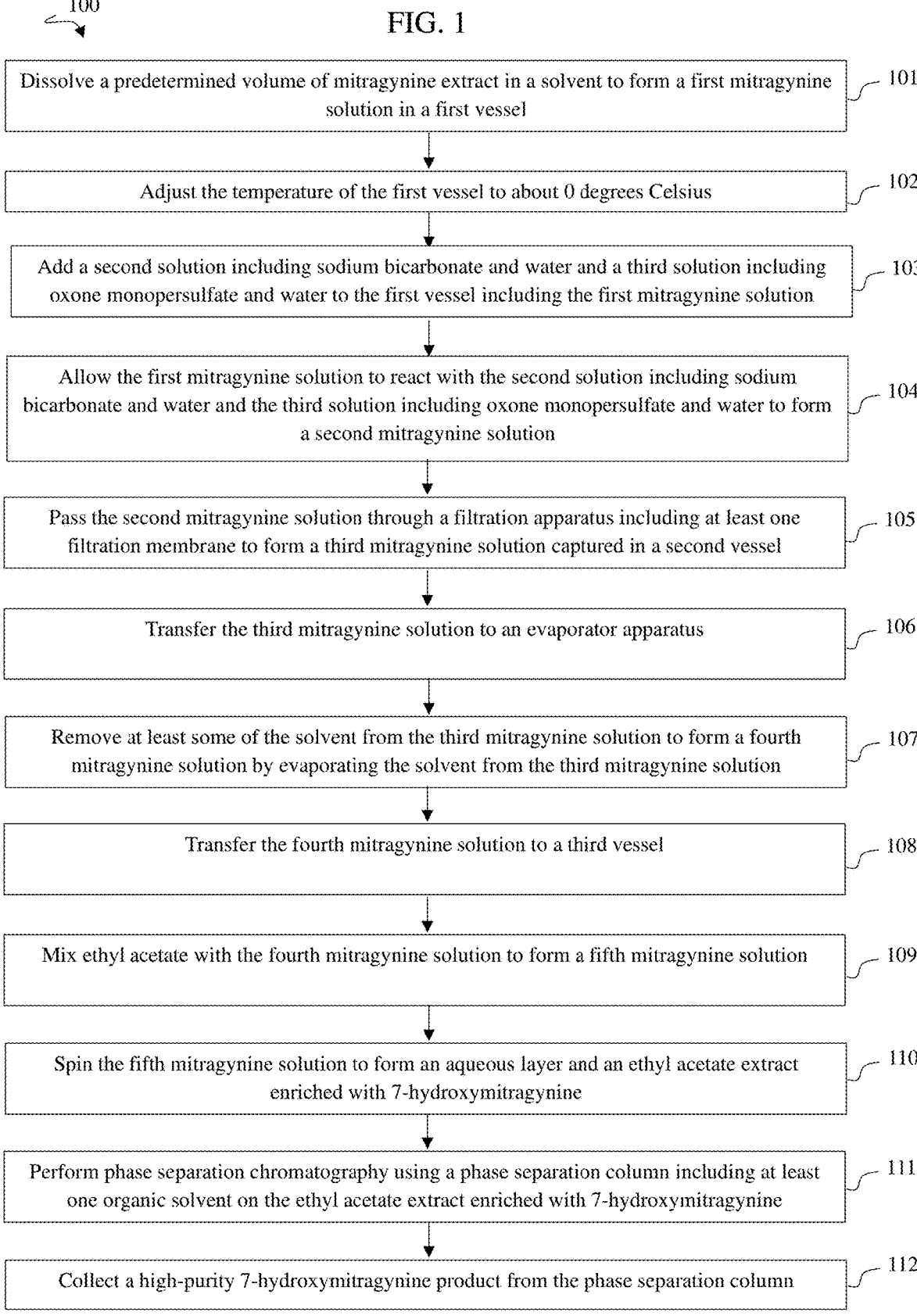

Dissolve a predetermined volume of mitragynine extract in a solvent to form a first mitragynine solution in a first vessel — 101

Adjust the temperature of the first vessel to about 0 degrees Celsius — 102

Add a second solution including sodium bicarbonate and water and a third solution including oxone monopersulfate and water to the first vessel including the first mitragynine solution — 103

Allow the first mitragynine solution to react with the second solution including sodium bicarbonate and water and the third solution including oxone monopersulfate and water to form a second mitragynine solution — 104

Pass the second mitragynine solution through a filtration apparatus including at least one filtration membrane to form a third mitragynine solution captured in a second vessel — 105

Transfer the third mitragynine solution to an evaporator apparatus — 106

Remove at least some of the solvent from the third mitragynine solution to form a fourth mitragynine solution by evaporating the solvent from the third mitragynine solution — 107

Transfer the fourth mitragynine solution to a third vessel — 108

Mix ethyl acetate with the fourth mitragynine solution to form a fifth mitragynine solution — 109

Spin the fifth mitragynine solution to form an aqueous layer and an ethyl acetate extract enriched with 7-hydroxymitragynine — 110

Perform phase separation chromatography using a phase separation column including at least one organic solvent on the ethyl acetate extract enriched with 7-hydroxymitragynine — 111

Collect a high-purity 7-hydroxymitragynine product from the phase separation column — 112

FIG. 2

200

Dissolve a predetermined volume of mitragynine extract in a solvent to form a first mitragynine solution in a first vessel ⟋ 201

Add a second solution including sodium bicarbonate and water and a third solution including oxone monopersulfate and water to the first vessel including the first mitragynine solution ⟋ 202

Allow the first mitragynine solution to react with the second solution including sodium bicarbonate and water and the third solution including oxone monopersulfate and water to form a second mitragynine solution ⟋ 203

Pass the second mitragynine solution through a filtration apparatus including at least one filtration membrane to form a third mitragynine solution captured in a second vessel ⟋ 204

Mix ethyl acetate with the third mitragynine solution to form a fourth mitragynine solution ⟋ 205

Spin the fourth mitragynine solution to form an aqueous layer and an ethyl acetate extract enriched with 7-hydroxymitragynine ⟋ 206

Perform phase separation chromatography using a phase separation column including at least one organic solvent on the ethyl acetate extract enriched with 7-hydroxymitragynine ⟋ 207

Collect a high-purity 7-hydroxymitragynine product from the phase separation column ⟋ 208

FIG. 3

300

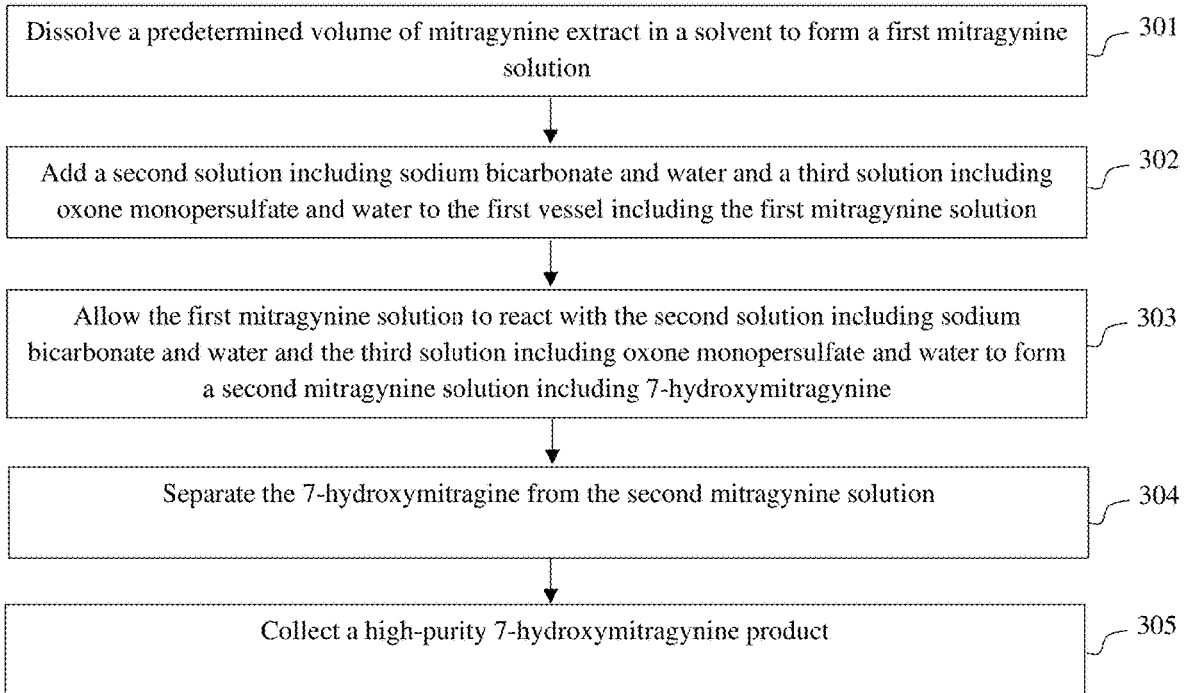

| Dissolve a predetermined volume of mitragynine extract in a solvent to form a first mitragynine solution | 301 |

| Add a second solution including sodium bicarbonate and water and a third solution including oxone monopersulfate and water to the first vessel including the first mitragynine solution | 302 |

| Allow the first mitragynine solution to react with the second solution including sodium bicarbonate and water and the third solution including oxone monopersulfate and water to form a second mitragynine solution including 7-hydroxymitragynine | 303 |

| Separate the 7-hydroxymitragine from the second mitragynine solution | 304 |

| Collect a high-purity 7-hydroxymitragynine product | 305 |

FIG. 4

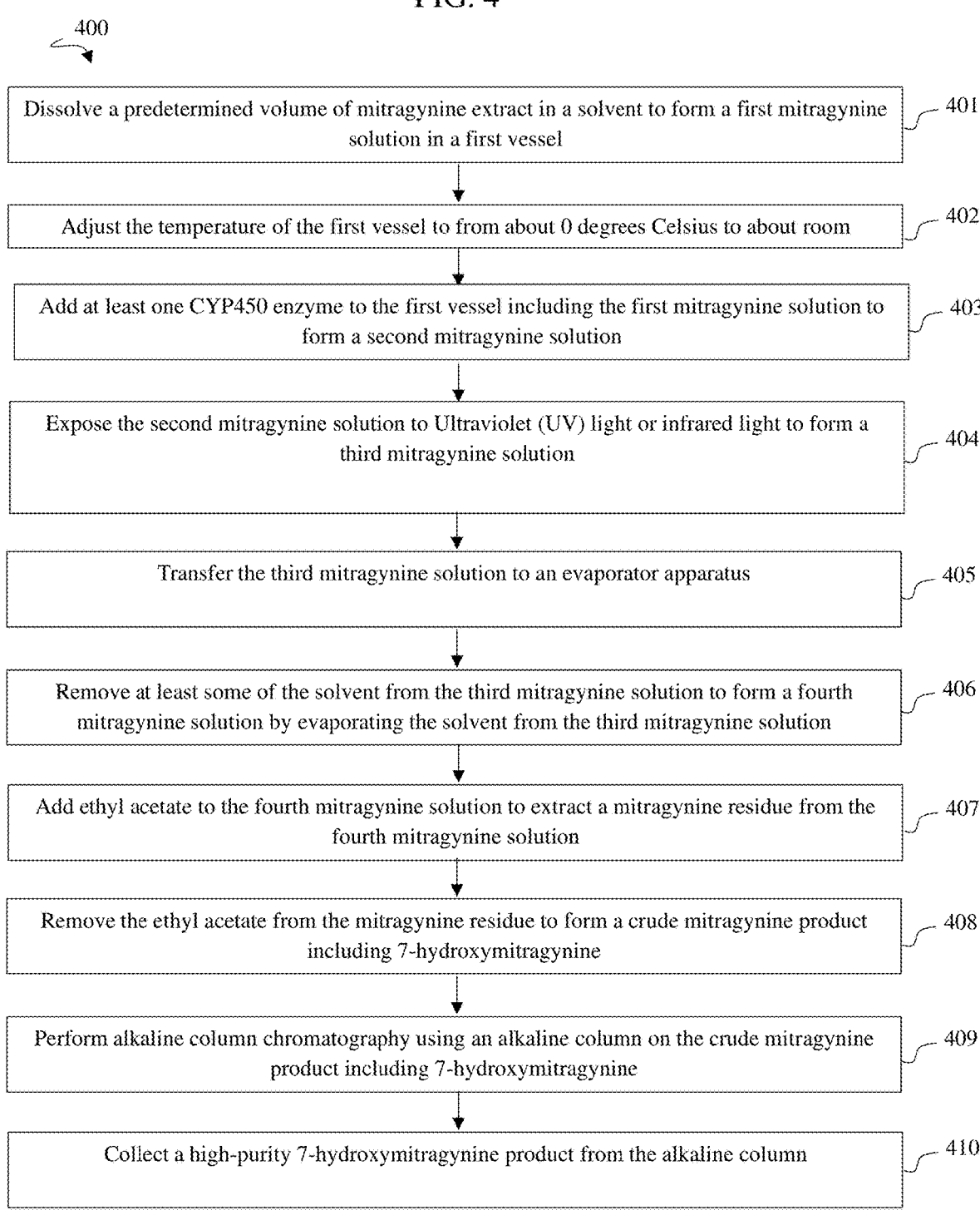

400

Dissolve a predetermined volume of mitragynine extract in a solvent to form a first mitragynine solution in a first vessel — 401

Adjust the temperature of the first vessel to from about 0 degrees Celsius to about room — 402

Add at least one CYP450 enzyme to the first vessel including the first mitragynine solution to form a second mitragynine solution — 403

Expose the second mitragynine solution to Ultraviolet (UV) light or infrared light to form a third mitragynine solution — 404

Transfer the third mitragynine solution to an evaporator apparatus — 405

Remove at least some of the solvent from the third mitragynine solution to form a fourth mitragynine solution by evaporating the solvent from the third mitragynine solution — 406

Add ethyl acetate to the fourth mitragynine solution to extract a mitragynine residue from the fourth mitragynine solution — 407

Remove the ethyl acetate from the mitragynine residue to form a crude mitragynine product including 7-hydroxymitragynine — 408

Perform alkaline column chromatography using an alkaline column on the crude mitragynine product including 7-hydroxymitragynine — 409

Collect a high-purity 7-hydroxymitragynine product from the alkaline column — 410

FIG. 5

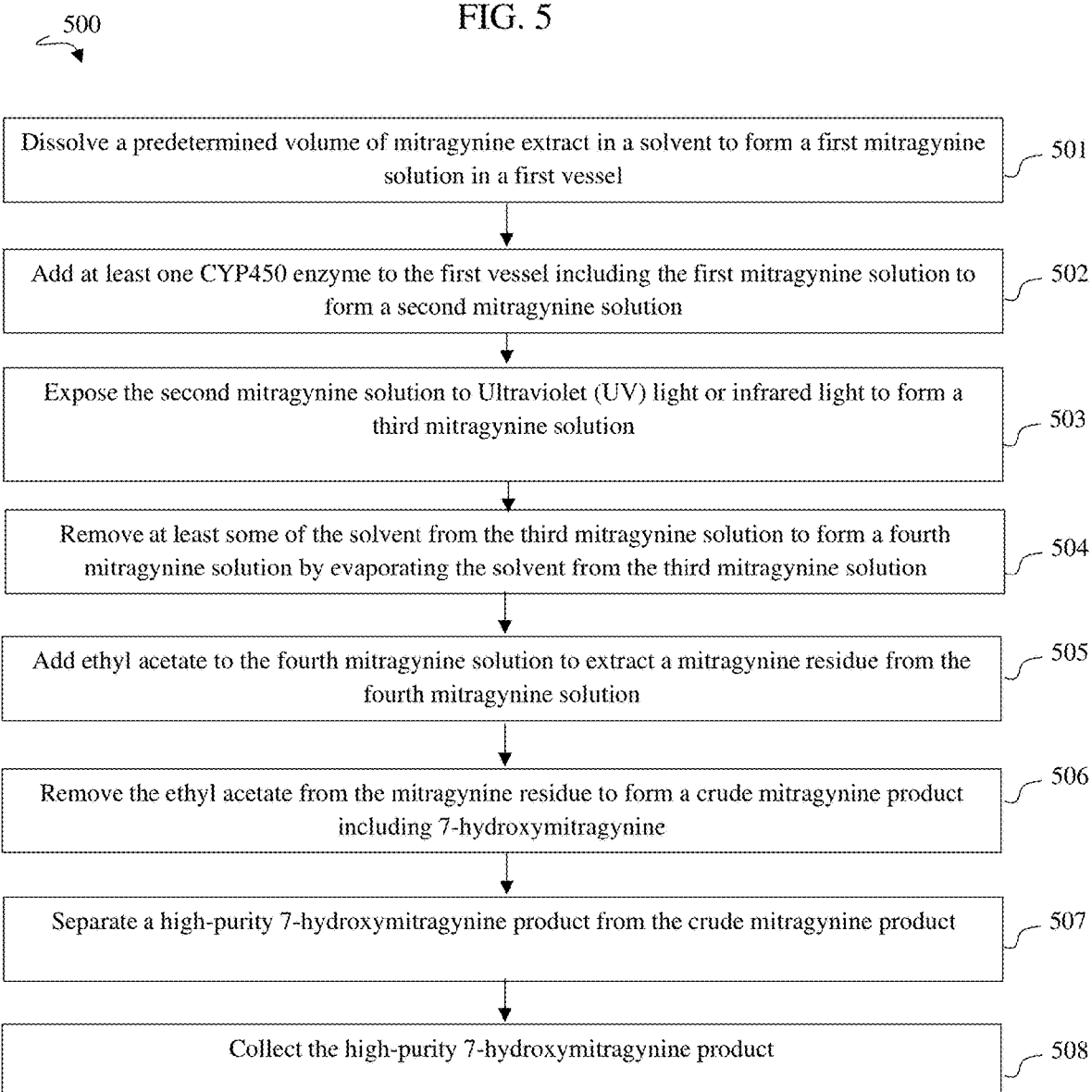

500

Dissolve a predetermined volume of mitragynine extract in a solvent to form a first mitragynine solution in a first vessel — 501

Add at least one CYP450 enzyme to the first vessel including the first mitragynine solution to form a second mitragynine solution — 502

Expose the second mitragynine solution to Ultraviolet (UV) light or infrared light to form a third mitragynine solution — 503

Remove at least some of the solvent from the third mitragynine solution to form a fourth mitragynine solution by evaporating the solvent from the third mitragynine solution — 504

Add ethyl acetate to the fourth mitragynine solution to extract a mitragynine residue from the fourth mitragynine solution — 505

Remove the ethyl acetate from the mitragynine residue to form a crude mitragynine product including 7-hydroxymitragynine — 506

Separate a high-purity 7-hydroxymitragynine product from the crude mitragynine product — 507

Collect the high-purity 7-hydroxymitragynine product — 508

FIG. 6

 600

| | |
|---|---|
| Dissolve a predetermined volume of mitragynine extract in a solvent to form a first mitragynine solution | 601 |
| Add an enzyme to the first vessel including the first mitragynine solution to form a second mitragynine solution | 602 |
| Expose the second mitragynine solution to light to form a third mitragynine solution | 603 |
| Remove at least some of the solvent from the third mitragynine solution to form a fourth mitragynine solution | 604 |
| Add an organic solvent to the fourth mitragynine solution to extract a mitragynine residue from the fourth mitragynine solution | 605 |
| Remove the organic solvent from the mitragynine residue to form a crude mitragynine product including 7-hydroxymitragynine | 606 |
| Separate a high-purity 7-hydroxymitragynine product from the crude mitragynine product | 607 |
| Collect the high-purity 7-hydroxymitragynine product | 608 |

FIG. 7

700

| Dissolve a predetermined volume of mitragynine extract in a solvent including tetrahydrofuran (THF) and water to form a first mitragynine solution | 701 |

| Cool the first mitragynine solution to a temperature ranging from about -5 degrees Celsius to about 5 degrees Celsius | 702 |

| Add PIFA to the first mitragynine solution | 703 |

| Allow the first mitragynine solution to react with the solvent and the PIFA to form a second mitragynine solution | 704 |

| Quench the second mitragynine solution with a saturated sodium bicarbonate solution to form a third mitragynine solution | 705 |

| Add ethyl acetate to the third mitragynine solution to extract a crude mitragynine product including 7-hydroxymitragynine | 706 |

| Perform alkaline column chromatography using an alkaline column on the crude mitragynine product including 7-hydroxymitragynine | 707 |

| Collect a high-purity 7-hydroxymitragynine product from the alkaline column | 708 |

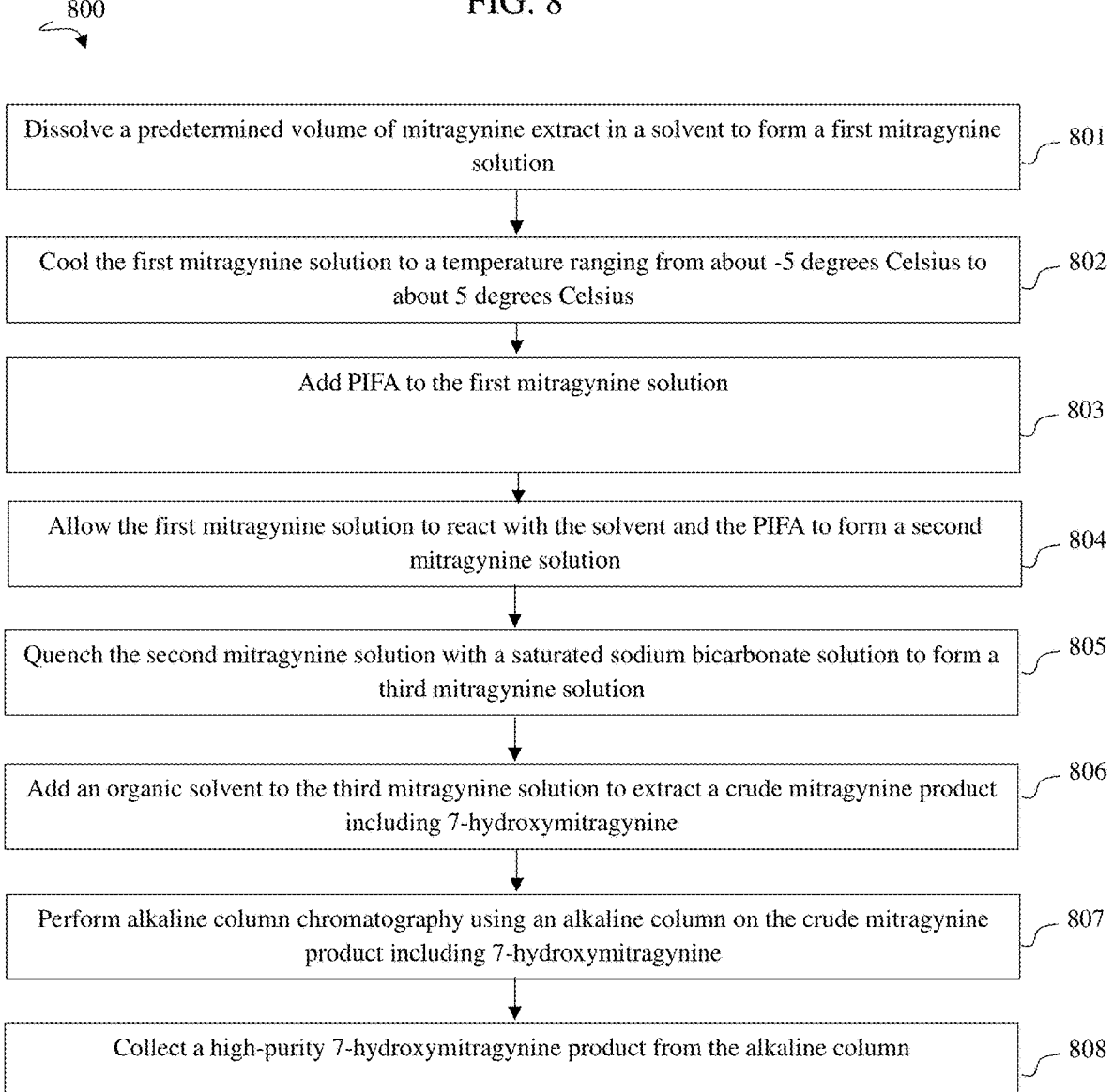

Dissolve a predetermined volume of mitragynine extract in a solvent to form a first mitragynine solution — 801

Cool the first mitragynine solution to a temperature ranging from about -5 degrees Celsius to about 5 degrees Celsius — 802

Add PIFA to the first mitragynine solution — 803

Allow the first mitragynine solution to react with the solvent and the PIFA to form a second mitragynine solution — 804

Quench the second mitragynine solution with a saturated sodium bicarbonate solution to form a third mitragynine solution — 805

Add an organic solvent to the third mitragynine solution to extract a crude mitragynine product including 7-hydroxymitragynine — 806

Perform alkaline column chromatography using an alkaline column on the crude mitragynine product including 7-hydroxymitragynine — 807

Collect a high-purity 7-hydroxymitragynine product from the alkaline column — 808

FIG. 9

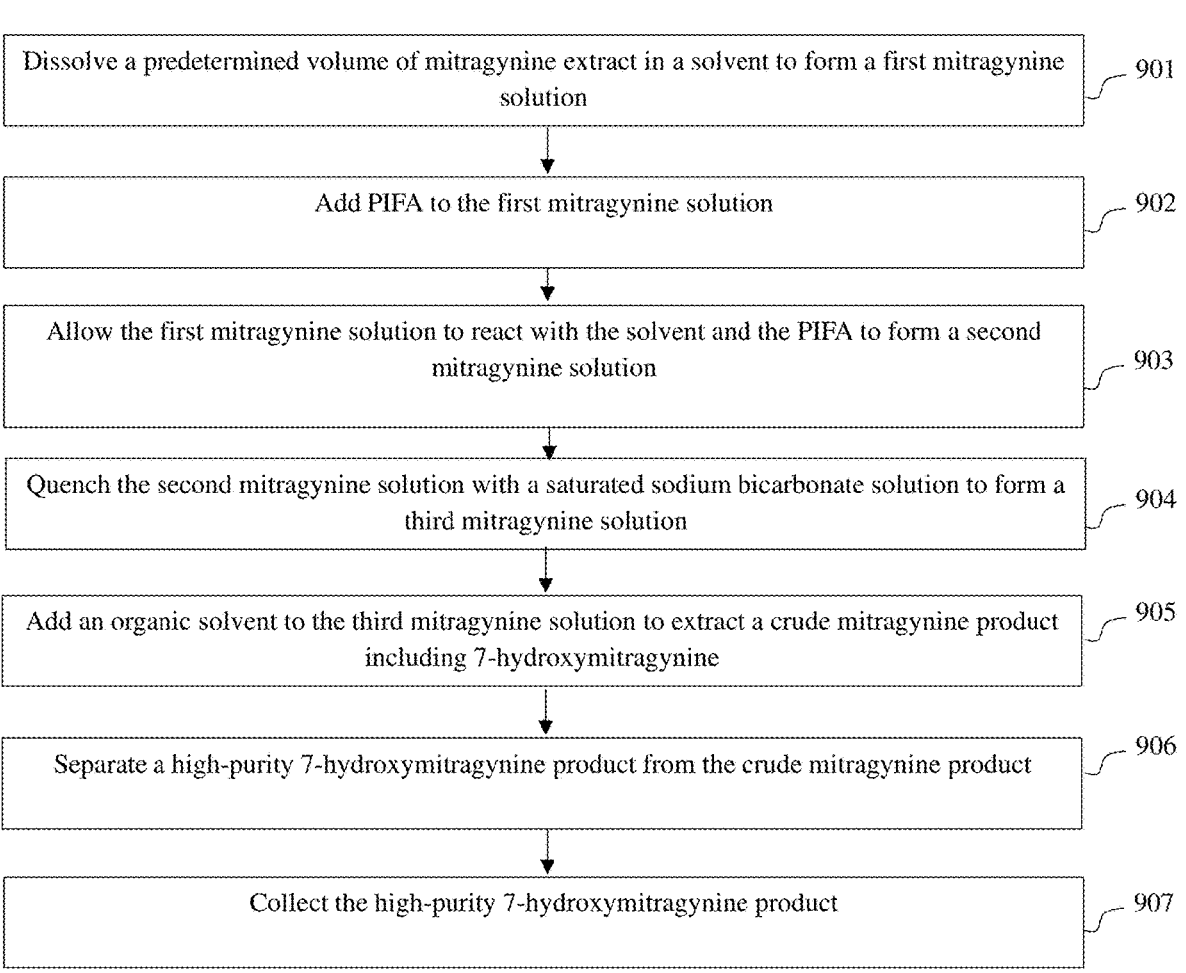

900

Dissolve a predetermined volume of mitragynine extract in a solvent to form a first mitragynine solution — 901

Add PIFA to the first mitragynine solution — 902

Allow the first mitragynine solution to react with the solvent and the PIFA to form a second mitragynine solution — 903

Quench the second mitragynine solution with a saturated sodium bicarbonate solution to form a third mitragynine solution — 904

Add an organic solvent to the third mitragynine solution to extract a crude mitragynine product including 7-hydroxymitragynine — 905

Separate a high-purity 7-hydroxymitragynine product from the crude mitragynine product — 906

Collect the high-purity 7-hydroxymitragynine product — 907

METHOD OF CONVERTING MITRAGYNINE TO 7-HYDROXYMITRAGYNINE

CROSS-REFERENCE TO RELATED APPLICATIONS

The present application is a continuation of U.S. patent application Ser. No. 18/664,689, filed on May 15, 2024. The entire contents of which are incorporated by reference herein.

FIELD

The present disclosure relates to mitragynine and 7-hydroxymitragynine and, more particularly, to a method of converting mitragynine to 7-hydroxymitragynine.

BACKGROUND

Mitragynine is a principal psychoactive alkaloid of the kratom plant (*Mitragyna speciosa*), exhibiting analgesic properties. However, its derivative, 7-hydroxymitragynine, is significantly more potent and of higher pharmacological interest. Existing methods of conversion are typically inefficient, requiring harsh conditions or yielding low conversion rates.

SUMMARY

The systems and methods described herein provide an efficient, controlled, and reproducible method for converting mitragynine to 7-hydroxymitragynine. As an example, a reactor system with precise temperature and mixing controls can be employed to optimize the conversion rate and purity of the product.

Provided in accordance with aspects of the present disclosure is a method of converting mitragynine to 7-hydroxymitragynine including dissolving a predetermined volume of mitragynine extract in a solvent to form a first mitragynine solution in a first vessel. The temperature of the first vessel is adjusted to be about 0 degrees Celsius. A second solution including sodium bicarbonate and water and a third solution including oxone monopersulfate and water are added to the first vessel including the first mitragynine solution. The first mitragynine solution is allowed to react with the second solution including sodium bicarbonate and water and the third solution including oxone monopersulfate and water to form a second mitragynine solution. The second mitragynine solution is passed through a filtration apparatus including a filtration membrane to form a third mitragynine solution captured in a second vessel. The third mitragynine solution is transferred to an evaporator apparatus. At least some of the solvent is removed from the third mitragynine solution to form a fourth mitragynine solution by evaporating the solvent from the third mitragynine solution. The fourth mitragynine solution is transferred to a third vessel. Ethyl acetate is mixed with the fourth mitragynine solution to form a fifth mitragynine solution. The fifth mitragynine solution is spun to form an aqueous layer and an ethyl acetate extract enriched with 7-hydroxymitragynine. Phase separation chromatography using a phase separation column including at least one organic solvent is performed on the ethyl acetate extract enriched with 7-hydroxymitragynine. A high-purity 7-hydroxymitragynine product is collected from the phase separation column.

In an aspect of the present disclosure, the first vessel is maintained at the temperature of about 0 degrees Celsius in a reactor including a chiller configured to maintain a temperature of the first vessel.

In an aspect of the present disclosure, the reactor is a double jacketed stainless steel reactor.

In an aspect of the present disclosure, the reactor includes a stirrer. The second solution includes sodium bicarbonate and water and the third solution including oxone monopersulfate and water are added to the first vessel simultaneously while being continuously stirred by the stirrer of the reactor.

In an aspect of the present disclosure, the reaction between the first mitragynine solution and the second solution including sodium bicarbonate and water and the third solution including oxone monopersulfate and water is allowed to proceed for 60-minutes while a reaction chamber of the reactor is maintained with an argon atmosphere. The first vessel is maintained at about 0 degrees Celsius for the duration of the 60-minutes by the reactor.

In an aspect of the present disclosure, the filtration membrane of the filtration apparatus includes a micron scale separation screen and at least one layer of filter paper secured by an O-ring.

In an aspect of the present disclosure, forming the fourth mitragynine solution includes removing at least 99% of the solvent by volume from the third mitragynine solution by evaporating the solvent from the third mitragynine solution.

In an aspect of the present disclosure, forming the fourth mitragynine solution includes removing at least 99% of the solvent by volume from the third mitragynine solution by evaporating the solvent from the third mitragynine solution.

In an aspect of the present disclosure, the sodium bicarbonate solution is prepared by stirring sodium bicarbonate into water in a first preparation vessel, and wherein the oxone monopersulfate solution is separately prepared by stirring oxone monopersulfate into water in a second preparation vessel.

In an aspect of the present disclosure, the evaporating is performed using a rotary evaporator.

In an aspect of the present disclosure, the rotatory evaporator is set at about 50 degrees Celsius and about 60 revolutions per minute (RPM) under vacuum conditions.

In an aspect of the present disclosure, the fifth mitragynine solution spun at least once at about 200 RPM and then allowed to settle for about 3 minutes.

In an aspect of the present disclosure, the fifth mitragynine solution is iteratively spun at about 200 RPM and then allowed to settle for about 3 minutes from 2 to 6 times.

In an aspect of the present disclosure, the aqueous layer is discarded.

In an aspect of the present disclosure, the organic solvent includes a blend of organic solvents each dissolved in a ratio of 0.5-10 ml organic solvent to 1 g mitragynine.

In an aspect of the present disclosure, residual organic solvents of the blend of organic solvents are removed from the phase separation column under vacuum conditions to yield the high-purity 7-hydroxymitragynine product from the phase separation column.

In an aspect of the present disclosure, the organic solvent is removed from the phase separation column by a vacuum oven maintained at from 25 degrees Celsius to 75 degrees Celsius.

In an aspect of the present disclosure, the high-purity 7-hydroxymitragynine product contains at least 95% 7-hydroxymitragynine and no more than 5% mitragynine.

Provided in accordance with aspects of the present disclosure is a method of converting mitragynine to 7-hydroxymitragynine including dissolving a predetermined volume of mitragynine extract in a solvent to form a first mitragynine solution in a first vessel. The method includes adding a second solution including sodium bicarbonate and water and a third solution including oxone monopersulfate and water to the first vessel including the first mitragynine solution. The first mitragynine solution is allowed to react with the second solution including sodium bicarbonate and water and the third solution including oxone monopersulfate and water to form a second mitragynine solution. The second mitragynine solution is passed through a filtration apparatus including at least one filtration membrane to form a third mitragynine solution captured in a second vessel.

Ethyl acetate is mixed with the third mitragynine solution to form a fourth mitragynine solution. The fourth mitragynine solution is spun to form an aqueous layer and an ethyl acetate extract enriched with 7-hydroxymitragynine. The method includes performing phase separation chromatography using a phase separation column including an organic solvent on the ethyl acetate extract enriched with 7-hydroxymitragynine. A high-purity 7-hydroxymitragynine product is collected from the phase separation column.

Provided in accordance with aspects of the present disclosure is a method of converting mitragynine to 7-hydroxymitragynine including dissolving a predetermined volume of mitragynine extract in a solvent to form a first mitragynine solution. The method includes adding a second solution including sodium bicarbonate and water and a third solution including oxone monopersulfate and water to the first vessel including the first mitragynine solution. The first mitragynine solution is allowed to react with the second solution including sodium bicarbonate and water and the third solution including oxone monopersulfate and water to form a second mitragynine solution including 7-hydroxymitragynine. The method includes separating the 7-hydroxymitragine from the second mitragynine solution and collecting a high-purity 7-hydroxymitragynine product.

Provided in accordance with aspects of the present disclosure is a method of modification of mitragynine to 7-hydroxymitragynine including dissolving a predetermined volume of mitragynine extract in a solvent to form a first mitragynine solution in a first vessel. The temperature of the first vessel is adjusted to be from about 0 degrees Celsius to about room temperature. At least one CYP450 enzyme is added to the first vessel including the first mitragynine solution to form a second mitragynine solution. The second mitragynine solution is exposed to Ultraviolet (UV) light or infrared light to form a third mitragynine solution. The third mitragynine solution is transferred to an evaporator apparatus. At least some of the solvent is removed from the third mitragynine solution to form a fourth mitragynine solution by evaporating the solvent from the third mitragynine solution. Ethyl acetate is added to the fourth mitragynine solution to extract a mitragynine residue from the fourth mitragynine solution. The ethyl acetate is removed from the mitragynine residue to form a crude mitragynine product including 7-hydroxymitragynine. Alkaline column chromatography using an alkaline column is performed on the crude mitragynine product including 7-hydroxymitragynine. A high-purity 7-hydroxymitragynine product is collected from the alkaline column.

In an aspect of the present disclosure, the solvent is methanol, acetone, water, tetrahydrofuran, or acetic acid.

In an aspect of the present disclosure, the CYP450 enzyme is generated by a bacteria or a yeast.

In an aspect of the present disclosure, the method includes adding a CYP450 substrate to the first vessel to form the second mitragynine solution.

In an aspect of the present disclosure, the CYP450 substrate is a substrate that interacts with UV light or infrared light.

In an aspect of the present disclosure, the CYP450 substrate is 7-Ethoxyresorufin.

In an aspect of the present disclosure, the CYP450 enzyme includes CYP1A1 or CYP1A2.

In an aspect of the present disclosure, the CYP450 substrate is ethoxyquin, theophylline, benzo[a]pyrene, acetanilide or aflatoxin A1.

In an aspect of the present disclosure, the UV light is in a wavelength range of from about 150 nm to about 350 nm.

In an aspect of the present disclosure, the second mitragynine solution is exposed to the UV light or the infrared light while being continuously stirred.

In an aspect of the present disclosure, at least one of ozone, oxygen, or hydrogen peroxide is added to the second mitragynine solution to form the third mitragynine solution.

In an aspect of the present disclosure, the ozone or oxygen is aerated into the second mitragynine solution.

In an aspect of the present disclosure, a chemical that emits singlet oxygen in the presence of UV light is added to the second mitragynine solution to form the third mitragynine solution.

In an aspect of the present disclosure, the chemical that emits singlet oxygen in the presence of UV light is a sodium salt or Rose Bengal.

In an aspect of the present disclosure, forming the fourth mitragynine solution includes removing from about 60% to about 99% of the solvent by volume from the third mitragynine solution by evaporating the solvent from the third mitragynine solution.

In an aspect of the present disclosure, the method includes washing the mitragynine residue.

In an aspect of the present disclosure, the alkaline column is a silica gel column modified with triethylamine and petroleum ether.

In an aspect of the present disclosure, the silica gel column is eluted with a 1:1 mixture of ethyl acetate and petroleum.

Provided in accordance with aspects of the present disclosure is a method of modification of mitragynine to 7-hydroxymitragynine including dissolving a predetermined volume of mitragynine extract in a solvent to form a first mitragynine solution in a first vessel. At least one CYP450 enzyme is added to the first vessel including the first mitragynine solution to form a second mitragynine solution. The method includes exposing the second mitragynine solution to Ultraviolet (UV) light or infrared light to form a third mitragynine solution. At least some of the solvent is removed from the third mitragynine solution to form a fourth mitragynine solution by evaporating the solvent from the third mitragynine solution. Ethyl acetate is added to the fourth mitragynine solution to extract a mitragynine residue from the fourth mitragynine solution. The ethyl acetate is removed from the mitragynine residue to form a crude mitragynine product including 7-hydroxymitragynine. The method includes separating a high-purity 7-hydroxymitragynine product from the crude mitragynine product and collecting the high-purity 7-hydroxymitragynine product.

Provided in accordance with aspects of the present disclosure is a method of modification of mitragynine to 7-hydroxymitragynine including dissolving a predetermined volume of mitragynine extract in a solvent to form a first mitragynine solution in a first vessel. The method includes adding an enzyme to the first vessel including the first mitragynine solution to form a second mitragynine solution. The second mitragynine solution is exposed to light to form a third mitragynine solution. At least some of the solvent is removed from the third mitragynine solution to form a fourth mitragynine solution. An organic solvent is added to the fourth mitragynine solution to extract a mitragynine residue from the fourth mitragynine solution. The organic solvent is removed from the mitragynine residue to form a crude mitragynine product including 7-hydroxymitragynine. The method includes separating a high-purity 7-hydroxymitragynine product from the crude mitragynine product and collecting the high-purity 7-hydroxymitragynine product.

Provided in accordance with aspects of the present disclosure is a method of synthesizing 7-hydroxymitragynine including dissolving a predetermined volume of mitragynine extract in a solvent including tetrahydrofuran (THF) and water to form a first mitragynine solution. The first mitragynine solution is cooled to a temperature ranging from about-5 degrees Celsius to about 5 degrees Celsius. PIFA is added to the first mitragynine solution. The first mitragynine solution is allowed to react with the solvent and the PIFA to form a second mitragynine solution. The second mitragynine solution is quenched with a saturated sodium bicarbonate solution to form a third mitragynine solution. Ethyl acetate is added to the third mitragynine solution to extract a crude mitragynine product including 7-hydroxymitragynine. Alkaline column chromatography using an alkaline column is performed on the crude mitragynine product including 7-hydroxymitragynine. A high-purity 7-hydroxymitragynine product is collected from the alkaline column.

In an aspect of the present disclosure, the predetermined volume of mitragynine extract is dissolved in the solvent including THF and water under an argon atmosphere.

In an aspect of the present disclosure, the first mitragynine solution is allowed to react with the solvent and the PIFA for from about 2 hours to about 10 hours.

In an aspect of the present disclosure, quenching the second mitragynine solution includes adjusting the pH of the second mitragynine solution to be from about 7 to about 9.5.

In an aspect of the present disclosure, extracting the crude mitragynine product including 7-hydroxymitragynine includes washing the crude mitragynine product including 7-hydroxymitragynine with saline.

In an aspect of the present disclosure, the washed crude mitragynine product including 7-hydroxymitragynine is dried over anhydrous sodium sulfate.

In an aspect of the present disclosure, the alkaline column is a silica gel column modified with triethylamine and petroleum ether.

In an aspect of the present disclosure, the silica gel column is eluted with a 1:1 mixture of ethyl acetate and petroleum ether.

In an aspect of the present disclosure, the alkaline column has a pH ranging from about 7 to about 11.

In an aspect of the present disclosure, 0.1-2 g of PIFA is added to the first mitragynine solution per 1 g of mitragynine extract.

In an aspect of the present disclosure, the alkaline column is prepared by rinsing silica gel with triethylamine.

Provided in accordance with aspects of the present disclosure is a method of synthesizing 7-hydroxymitragynine including dissolving a predetermined volume of mitragynine extract in a solvent to form a first mitragynine solution. The method includes cooling the first mitragynine solution to a temperature ranging from about-5 degrees Celsius to about 5 degrees Celsius. PIFA is added to the first mitragynine solution. The first mitragynine solution is allowed to react with the solvent and the PIFA to form a second mitragynine solution. The second mitragynine solution is quenched with a saturated sodium bicarbonate solution to form a third mitragynine solution. The method includes adding an organic solvent to the third mitragynine solution to extract a crude mitragynine product including 7-hydroxymitragynine. Alkaline column chromatography using an alkaline column is performed on the crude mitragynine product including 7-hydroxymitragynine. A high-purity 7-hydroxymitragynine product is collected from the alkaline column.

Provided in accordance with aspects of the present disclosure is a method of synthesizing 7-hydroxymitragynine including dissolving a predetermined volume of mitragynine extract in a solvent to form a first mitragynine solution. PIFA is added to the first mitragynine solution. The method includes allowing the first mitragynine solution to react with the solvent and the PIFA to form a second mitragynine solution. The second mitragynine solution is quenched with a saturated sodium bicarbonate solution to form a third mitragynine solution. An organic solvent is added to the third mitragynine solution to extract a crude mitragynine product including 7-hydroxymitragynine. The method includes separating a high-purity 7-hydroxymitragynine product from the crude mitragynine product and collecting the high-purity 7-hydroxymitragynine product.

Provided in accordance with aspects of the present disclosure is a method of administering a therapeutic formulation including administering a compound having the structure:

in which R2 is —H or -alkyl, R3 is —H or -alkyl, and R4 is —H or -alkyl. The method includes administering a potentiator of the compound. The potentiator is configured to enhance analgesic efficacy of the compound.

In an aspect of the present disclosure, the potentiator is agmatine.

In an aspect of the present disclosure, the potentiator is liposomal vitamin C.

In an aspect of the present disclosure, the potentiator is a tyramine.

In an aspect of the present disclosure, the potentiator is octopamine, dopamine, or norepinephrine.

In an aspect of the present disclosure, the potentiator is a CYP450 inhibitor.

In an aspect of the present disclosure, the CYP450 inhibitor is grapefruit juice, ketoconazole, or erythromycin.

In an aspect of the present disclosure, the potentiator is an NMDA receptor agonist.

In an aspect of the present disclosure, the potentiator is an antidepressant.

In an aspect of the present disclosure, the potentiator is a GABA agonist.

In an aspect of the present disclosure, the potentiator is a muscle relaxant.

In an aspect of the present disclosure, the potentiator is an antihistamine.

Provided in accordance with aspects of the present disclosure is a therapeutic formulation including a compound having the structure:

in which R2 is —H or -alkyl, R3 is —H or -alkyl, and R4 is —H or -alkyl. The therapeutic formulation includes a potentiator of the compound. The potentiator is configured to enhance analgesic efficacy of the compound.

In an aspect of the present disclosure, the potentiator of the therapeutic formulation is agmatine.

In an aspect of the present disclosure, the potentiator of the therapeutic formulation is liposomal vitamin C.

In an aspect of the present disclosure, the potentiator of the therapeutic formulation is a tyramine.

In an aspect of the present disclosure, the potentiator of the therapeutic formulation is octopamine, dopamine, or norepinephrine.

In an aspect of the present disclosure, the potentiator of the therapeutic formulation is a CYP450 inhibitor.

In an aspect of the present disclosure, the potentiator of the therapeutic formulation is grapefruit juice, ketoconazole, or erythromycin.

In an aspect of the present disclosure, the potentiator of the therapeutic formulation is the potentiator is an NMDA receptor agonist.

In an aspect of the present disclosure, the potentiator of the therapeutic formulation is an antidepressant.

In an aspect of the present disclosure, the potentiator of the therapeutic formulation is a GABA agonist.

In an aspect of the present disclosure, the potentiator of the therapeutic formulation is a muscle relaxant.

In an aspect of the present disclosure, the potentiator of the therapeutic formulation is an antihistamine.

Provided in accordance with aspects of the present disclosure is a carrier for administering a therapeutic formulation including a compound having the structure:

8 in which R2 is —H or -alkyl, R3 is —H or -alkyl, and R4 is —H or -alkyl. The carrier includes a potentiator of the compound. The potentiator is configured to enhance analgesic efficacy of the compound. The carrier is configured to administer the compound and the potentiator to a user.

In an aspect of the present disclosure, the potentiator of compound included in the carrier is agmatine, liposomal vitamin C, a tyramine, octopamine, dopamine, norepinephrine, a CYP450 inhibitor, grapefruit juice, ketoconazole, or erythromycin, an NMDA receptor agonist, an antidepressant, a GABA agonist, a muscle relaxant, or an antihistamine.

In an aspect of the present disclosure, the carrier is configured to administer the compound and the potentiator to the user by oral delivery, transdermal delivery, parenteral delivery, pulmonary delivery, inhalation delivery, intramuscular delivery, subcutaneous delivery, rectal delivery, or topical delivery.

In an aspect of the present disclosure, the carrier is a transdermal patch.

In an aspect of the present disclosure, the transdermal patch is a slow release patch, a reservoir patch, a matrix patch, a drug-in-adhesive patch, a vapor patch, a microneedle patch, a reservoir-in-matrix patch, or an active transdermal patch.

In an aspect of the present disclosure, the carrier is an inhaler or a vaporizer.

In an aspect of the present disclosure, the carrier includes a cartridge configured to hold the compound and the potentiator of the compound. The cartridge is configured to be operably coupled with the inhaler or the vaporizer.

In an aspect of the present disclosure, the carrier is a tablet, a tincture, a suspension, or an emulsion.

In an aspect of the present disclosure, the carrier includes lactose, sucrose, gelatine, or agar.

In an aspect of the present disclosure, the carrier includes saline, or a dextrose solution.

In an aspect of the present disclosure, the carrier includes a binder, a lubricant, a dilutant, a disintegrating agent, a coloring agent, a flavoring agent, or a preservative.

BRIEF DESCRIPTION OF THE DRAWINGS

Various aspects and features of the present disclosure are described hereinbelow with reference to the drawings wherein:

FIG. 1 is a flow chart illustrating a method of converting mitragynine to 7-hydroxymitragynine according to aspects of the present disclosure;

FIG. 2 is a flow chart illustrating another method of converting mitragynine to 7-hydroxymitragynine according to aspects of the present disclosure; and

FIG. 3 is a flow chart illustrating another method of converting mitragynine to 7-hydroxymitragynine according to aspects of the present disclosure.

FIG. 4 is a flow chart illustrating another method of converting mitragynine to 7-hydroxymitragynine according to aspects of the present disclosure;

FIG. 5 is a flow chart illustrating another method of converting mitragynine to 7-hydroxymitragynine according to aspects of the present disclosure; and FIG. 6 is a flow chart illustrating another method of converting mitragynine to 7-hydroxymitragynine according to aspects of the present disclosure.

FIG. 7 is a flow chart illustrating a method of synthesizing 7-hydroxymitragynine according to aspects of the present disclosure;

FIG. 8 is a flow chart illustrating another method of synthesizing 7-hydroxymitragynine according to aspects of the present disclosure; and FIG. 9 is a flow chart illustrating another method of synthesizing 7-hydroxymitragynine according to aspects of the present disclosure.

DETAILED DESCRIPTION

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Mitragynine has the chemical structure:

Mitragynine is a naturally occurring alkaloid compound found primarily in the leaves of *Mitragyna speciosa*, commonly known as kratom. It is structurally characterized as a monoterpene indole alkaloid, possessing a pentacyclic ring structure.

Chemically, mitragynine is classified as a methyl ester of a monoterpene indole, with the molecular formula C23H30N2O4.

Mitragynine exhibits opioid receptor agonist activity, particularly at μ-opioid receptors, contributing to its pharmacological effects.

Its pharmacological properties include analgesic, antinociceptive, and stimulating effects, making it a subject of interest for various pharmaceutical and therapeutic applications.

7-hydroxymitragynine has the chemical structure:

7-Hydroxymitragynine is a metabolite and active constituent derived from the biotransformation of mitragynine. Structurally, it is a derivative of mitragynine, featuring a hydroxyl group (—OH) substitution at the seventh carbon position on the indole ring.

Chemically, 7-hydroxymitragynine is characterized as a terpenoid indole alkaloid with the molecular formula C23H30N2O5.

It exhibits potent opioid receptor agonist activity, particularly at μ-opioid receptors, with significantly higher affinity and potency compared to mitragynine.

7-Hydroxymitragynine is associated with profound analgesic and antinociceptive effects, making it a key pharmacological target for the development of novel pain management medications.

Referring to FIG. 1, a method 100 of converting mitragynine to 7-hydroxymitragynine includes dissolving a predetermined volume of mitragynine extract in a solvent to form a first mitragynine solution in a first vessel 101. The temperature of the first vessel is adjusted to be about 0 degrees Celsius 102. A second solution including sodium bicarbonate and water and a third solution including oxone monopersulfate and water are added to the first vessel including the first mitragynine solution 103. The first mitragynine solution is allowed to react with the second solution including sodium bicarbonate and water and the third solution including oxone monopersulfate and water to form a second mitragynine solution 104. The second mitragynine solution is passed through a filtration apparatus including a filtration membrane to form a third mitragynine solution captured in a second vessel 105. The third mitragynine solution is transferred to an evaporator apparatus 106. At least some of the solvent is removed from the third mitragynine solution to form a fourth mitragynine solution by evaporating the solvent from the third mitragynine solution 107. The fourth mitragynine solution is transferred to a third vessel 108. Ethyl acetate is mixed with the fourth mitragynine solution to form a fifth mitragynine solution 109. The fifth mitragynine solution is spun to form an aqueous layer and an ethyl acetate extract enriched with 7-hydroxymitragynine 110. Phase separation chromatography using a phase separation column including at least one organic solvent is performed on the ethyl acetate extract enriched with 7-hydroxymitragynine 111. A high-purity 7-hydroxymitragynine product is collected from the phase separation column 112.

Exemplary Protocol for Converting Mitragynine to 7-Hydroxymitragynine.

Setup and Initial Preparation:

A 200 L double-jacketed stainless steel reactor equipped with a chiller is prepared and set to maintain a temperature of 0 degrees Celsius.

As an example, an argon atmosphere may be maintained in a reactor chamber of the stainless steel reactor.

Approximately 4 kg of mitragynine is weighed using an Ohaus analytical scale and subsequently added to the reactor containing 130 L of ACS grade acetone.

As an example, a mixture of mitragynine and solvent (e.g., ACS grade acetone) may be mixed in a vessel such that mitragynine is added in an amount ranging from 10% to 40% (more particularly about 30%) of the overall volume of the mixture.

Preparation of Reactant Solutions:

In separate glass beakers, 20 L of water is measured and used to prepare two solutions:

A sodium bicarbonate solution: 1400 grams of sodium bicarbonate are mixed into the water using an overhead stirrer.

An oxone monopersulfate solution: 4565 grams of an oxone monopersulfate are similarly mixed into another 20 L of water.

For example, 4565 grams of potassium peroxymonosulfate may be mixed into another 20 L of water.

Reactor Charging and Reaction Initiation:

Upon reaching the target temperature of 0 degrees Celsius in the reactor, a 60-minute timer is started.

Using peristaltic pumps, the sodium bicarbonate and oxone monopersulfate slurries are added simultaneously to the reactor at a rate of 5 L/min.

Completion of Reaction and Filtration:

After the 60-minute reaction period, the chiller and argon supply are turned off.

The reactor contents are then filtered using a Buchner funnel setup equipped with a 25-micron screen and an O-ring secured filter paper.

Solvent Evaporation:

The filtered solution is transferred to a 50 L rotary evaporator set at 50 degrees Celsius and 60 RPM under vacuum to remove approximately 130 L of solvent.

Separation:

The concentrated solution is transferred to a 200 L glass reactor and mixed with 50 L of ethyl acetate.

The mixture is rotated at 200 RPM for 3 minutes, allowed to settle, and the process repeated to enhance phase separation.

For example, rotation may be repeated, as described, from 1 to 6 times (e.g., 3 times).

The aqueous layer is discarded, leaving the ethyl acetate layer enriched with 7-hydroxymitragynine.

Purification:

The ethyl acetate extract, containing the alkaloid-rich solution, undergoes further purification through phase separation chromatography by means of an organic solvent or a blend of organic solvents dissolved in a ratio of 0.5-10 ml organic solvent to 1 g mitragynine.

Residual solvents are removed under vacuum to yield high-purity 7-hydroxymitragynine in a vacuum oven at 35 degrees Celsius to 75 degrees Celsius and under vacuum of medium (<1, >10-3 torr), high vacuum (<10-3, >10-8 torr), or ultra-high vacuum (<10-8 torr).

In an aspect of the present disclosure, the first vessel is maintained at the temperature of about 0 degrees Celsius in a reactor including a chiller configured to maintain a temperature of the first vessel.

The conversion of mitragynine to 7-hydroxymitragynine is an exothermic process, and thus maintaining a temperature of the reaction vessel has been found effective in maintaining the reaction rate during the reaction period (e.g., 60 minutes), as described herein.

The following considerations are important in maintaining vessel temperature during an exothermic reaction, such as for ensuring safety, controlling reaction kinetics, optimizing product quality, improving energy efficiency, and achieving process stability.

As an example, the reactor may be a double jacketed stainless steel reactor configured to control a temperature range therein.

In an aspect of the present disclosure, the reactor includes a stirrer. The second solution includes sodium bicarbonate and water and the third solution includes oxone monopersulfate and water are added to the first vessel simultaneously while being continuously stirred by the stirrer of the reactor.

In an aspect of the present disclosure, the reaction between the first mitragynine solution and the second solution including sodium bicarbonate and water and the third solution including oxone monopersulfate and water is allowed to proceed for 60-minutes while a reaction chamber of the reactor is maintained with an argon atmosphere. The first vessel is maintained at about 0 degrees Celsius for the duration of the 60-minutes by the reactor.

In an aspect of the present disclosure, the filtration membrane of the filtration apparatus includes a micron scale separation screen and at least one layer of filter paper secured by an O-ring.

In an aspect of the present disclosure, forming the fourth mitragynine solution includes removing at least 99% of the solvent by volume from the third mitragynine solution by evaporating the solvent from the third mitragynine solution.

In an aspect of the present disclosure, forming the fourth mitragynine solution includes removing at least 99% of the solvent by volume from the third mitragynine solution by evaporating the solvent from the third mitragynine solution.

In an aspect of the present disclosure, the sodium bicarbonate solution is prepared by stirring sodium bicarbonate into water in a first preparation vessel, and wherein the oxone monopersulfate solution is separately prepared by stirring oxone monopersulfate into water in a second preparation vessel.

In an aspect of the present disclosure, the evaporating is performed using a rotary evaporator.

In an aspect of the present disclosure, the rotatory evaporator is set at about 50 degrees Celsius and about 60 revolutions per minute (RPM) under vacuum conditions.

In an aspect of the present disclosure, the fifth mitragynine solution spun at least once at about 200 RPM and then allowed to settle for about 3 minutes.

In an aspect of the present disclosure, the fifth mitragynine solution is iteratively spun at about 200 RPM and then allowed to settle for about 3 minutes from 2 to 6 times.

In an aspect of the present disclosure, the aqueous layer is discarded.

In an aspect of the present disclosure, the organic solvent includes a blend of organic solvents each dissolved in a ratio of 0.5-10 ml organic solvent to 1 g mitragynine.

In an aspect of the present disclosure, residual organic solvents of the blend of organic solvents are removed from the phase separation column under vacuum conditions to yield the high-purity 7-hydroxymitragynine product from the phase separation column.

In an aspect of the present disclosure, the organic solvent is removed from the phase separation column by a vacuum oven maintained at from 25 degrees Celsius to 75 degrees Celsius.

In an aspect of the present disclosure, the high-purity 7-hydroxymitragynine product contains at least 95% 7-hydroxymitragynine and no more than 5% mitragynine.

Referring to FIG. 2, a method 200 of converting mitragynine to 7-hydroxymitragynine includes dissolving a predetermined volume of mitragynine extract in a solvent to form a first mitragynine solution in a first vessel 201. The method includes adding a second solution including sodium bicarbonate and water and a third solution including oxone monopersulfate and water to the first vessel including the first mitragynine solution 202. The first mitragynine solution is allowed to react with the second solution including sodium bicarbonate and water and the third solution including oxone monopersulfate and water to form a second mitragynine solution 203. The second mitragynine solution is passed through a filtration apparatus including at least one filtration membrane to form a third mitragynine solution captured in a second vessel 204. Ethyl acetate is mixed with the third mitragynine solution to form a fourth mitragynine solution 205. The fourth mitragynine solution is spun to form an aqueous layer and an ethyl acetate extract enriched with 7-hydroxymitragynine 206. The method includes performing phase separation chromatography using a phase separation column including an organic solvent on the ethyl acetate extract enriched with 7-hydroxymitragynine 207. A high-purity 7-hydroxymitragynine product is collected from the phase separation column 208.

Referring to FIG. 3, a method 300 of converting mitragynine to 7-hydroxymitragynine includes dissolving a predetermined volume of mitragynine extract in a solvent to form a first mitragynine solution 301. The method includes adding a second solution including sodium bicarbonate and water and a third solution including oxone monopersulfate and water to the first vessel including the first mitragynine solution 302. The first mitragynine solution is allowed to react with the second solution including sodium bicarbonate and water and the third solution including oxone monopersulfate and water to form a second mitragynine solution including 7-hydroxymitragynine 303. The method includes separating the 7-hydroxymitragine from the second mitragynine solution 304 and collecting a high-purity 7-hydroxymitragynine product 305.

Referring to FIG. 4, a method 400 of modification of mitragynine to 7-hydroxymitragynine includes dissolving a predetermined volume of mitragynine extract in a solvent to form a first mitragynine solution in a first vessel 401. The temperature of the first vessel is adjusted to be from about 0 degrees Celsius to about room temperature 402. At least one CYP450 enzyme is added to the first vessel including the first mitragynine solution to form a second mitragynine solution 403. The second mitragynine solution is exposed to Ultraviolet (UV) light or infrared light to form a third mitragynine solution 404. The third mitragynine solution is transferred to an evaporator apparatus 405. At least some of the solvent is removed from the third mitragynine solution to form a fourth mitragynine solution by evaporating the solvent from the third mitragynine solution 406. Ethyl acetate is added to the fourth mitragynine solution to extract a mitragynine residue from the fourth mitragynine solution 407. The ethyl acetate is removed from the mitragynine residue to form a crude mitragynine product including 7-hydroxymitragynine 408. Alkaline column chromatography using an alkaline column is performed on the crude mitragynine product including 7-hydroxymitragynine 409. A high-purity 7-hydroxymitragynine product is collected from the alkaline column 410.

Exemplary Protocol for Enzymatic Modification of Mitragynine to 7-Hydroxymitragynine:

Preparation of Mitragynine Solution:

A quantity of mitragynine is dissolved in a solvent such as methanol, acetone, water, tetrahydrofuran, or acetic acid. This solution is prepared to facilitate the subsequent enzymatic reaction.

As an example, mitragynine extract is dissolved in a ratio of 0.5-10 ml organic solvent to 1 g gram mitragynine.

The solvent may be an organic solvent or a blend of organic solvents dissolved in a ratio of 0.5-10 ml organic solvent to 1 g gram mitragynine. For example, a solvent blend of 50/50-95/5 of differing polarities (e.g., ethyl acetate/hexane) may be employed.

The enzymatic reaction utilizes UV light while in the presence of an enzyme that reacts with the CYP450 cytochrome.

Reactor Charging and Temperature Control:

The mitragynine solution is charged into a reactor. The temperature of the reactor is maintained between 0° C. and room temperature to optimize enzyme activity and stability.

Addition of CYP450 Enzyme and Substrate:

A predetermined amount of a CYP450 enzyme is added to the reactor. As an example, the CYP450 enzyme may be added at 0.1 g to 2 g ratio of enzyme to mitragynine.

As an example, the CYP450 enzyme could be generated by a bacteria or yeast.

A CYP450 substrate such as 7-Ethoxyresorufin which is known to interact with UV light may also be added to the enzyme/mitragynine mixture. The substrate can be a probe for enzyme activity or serve as a co-reactant.

UV Light Exposure and Stirring:

The reaction mixture is exposed to tuned UV light for a duration of 4 hours while stirring continuously.

The UV light wavelength and intensity are selected to maximize the enzyme activity and promote specific interactions between the enzyme and mitragynine. The UV light wavelength may be from 150-350 nm.

Ozone, oxygen and hydrogen peroxide may be added during this step to assist with hydroxylation.

A chemical known to emit singlet oxygen in the presence of light such as a sodium salt of Rose Bengal.

The sodium salt of Rose Bengal has also been observed to emit singlet oxygen in the presence of Infrared Light.

Ozone or oxygen may be aerated with air stones into solution.

As an example, hydrogen peroxide is added at a ratio from 0.25-2 ml to 1 g mitragynine.

Removal of Solvent:

Following the exposure to UV and/or Infrared light, the initial reaction solvent is removed via evaporation. This step concentrates the reaction mixture and prepares it for further extraction.

Extraction may be performed by means of an organic solvent or a blend of organic solvents dissolved in a ratio of 0.5-10 ml organic solvent to 1 g gram mitragynine.

The evaporation step may remove from 60-99% of the total solvent by volume from the reaction mixture.

Extraction and Washing:

The residue is then extracted with ethyl acetate. The organic layer obtained is washed with a saline solution multiple times (e.g., from 1 to 6 times, such as 3 times) to remove impurities and unreacted components, resulting in a purified product.

Product Recovery:

The crude product, including 7-hydroxymitragynine and other oxidized kratom alkaloid isomers and/or analogs, is recovered from the organic layer after the removal of ethyl acetate under reduced pressure.

Purification:

The crude product is subjected to alkaline column chromatography using a silica gel column modified with triethylamine and petroleum ether, eluted with a 1:1 mixture of ethyl acetate and light petroleum.

In an aspect of the present disclosure, the solvent is methanol, acetone, water, tetrahydrofuran, or acetic acid.

In an aspect of the present disclosure, the CYP450 enzyme is generated by a bacteria or a yeast.

In an aspect of the present disclosure, the method includes adding a CYP450 substrate to the first vessel to form the second mitragynine solution.

In an aspect of the present disclosure, the CYP450 substrate is a substrate that interacts with UV light or infrared light.

In an aspect of the present disclosure, the CYP450 substrate is 7-Ethoxyresorufin.

In an aspect of the present disclosure, the CYP450 enzyme includes CYP1A1 or CYP1A2.

In an aspect of the present disclosure, the CYP450 substrate is ethoxyquin, theophylline, benzo[a]pyrene, acetanilide or aflatoxin A1.

In an aspect of the present disclosure, the UV light is in a wavelength range of from about 150 nm to about 350 nm.

In an aspect of the present disclosure, the second mitragynine solution is exposed to the UV light or the infrared light while being continuously stirred.

In an aspect of the present disclosure, at least one of ozone, oxygen, or hydrogen peroxide is added to the second mitragynine solution to form the third mitragynine solution.

In an aspect of the present disclosure, the ozone or oxygen is aerated into the second mitragynine solution.

In an aspect of the present disclosure, a chemical that emits singlet oxygen in the presence of UV light is added to the second mitragynine solution to form the third mitragynine solution.

In an aspect of the present disclosure, the chemical that emits singlet oxygen in the presence of UV light is a sodium salt or Rose Bengal.

In an aspect of the present disclosure, forming the fourth mitragynine solution includes removing from about 60% to about 99% of the solvent by volume from the third mitragynine solution by evaporating the solvent from the third mitragynine solution.

In an aspect of the present disclosure, the method includes washing the mitragynine residue.

In an aspect of the present disclosure, the alkaline column is a silica gel column modified with triethylamine and petroleum ether.

In an aspect of the present disclosure, the silica gel column is eluted with a 1:1 mixture of ethyl acetate and petroleum.

Referring to FIG. 5, a method 500 of modification of mitragynine to 7-hydroxymitragynine includes dissolving a predetermined volume of mitragynine extract in a solvent to form a first mitragynine solution in a first vessel 501. At least one CYP450 enzyme is added to the first vessel including the first mitragynine solution to form a second mitragynine solution 502. The method includes exposing the second mitragynine solution to Ultraviolet (UV) light or infrared light to form a third mitragynine solution 503. At least some of the solvent is removed from the third mitragynine solution to form a fourth mitragynine solution by evaporating the solvent from the third mitragynine solution 504. Ethyl acetate is added to the fourth mitragynine solution to extract a mitragynine residue from the fourth mitragynine solution 505. The ethyl acetate is removed from the mitragynine residue to form a crude mitragynine product including 7-hydroxymitragynine 506. The method includes separating a high-purity 7-hydroxymitragynine product from the crude mitragynine product 507 and collecting the high-purity 7-hydroxymitragynine product 508.

Referring to FIG. 6, a method 600 of modification of mitragynine to 7-hydroxymitragynine includes dissolving a predetermined volume of mitragynine extract in a solvent to form a first mitragynine solution in a first vessel 601. The method includes adding an enzyme to the first vessel including the first mitragynine solution to form a second mitragynine solution 602. The second mitragynine solution is exposed to light to form a third mitragynine solution 603. At least some of the solvent is removed from the third mitragynine solution to form a fourth mitragynine solution 604. An organic solvent is added to the fourth mitragynine solution to extract a mitragynine residue from the fourth mitragynine solution 605. The organic solvent is removed from the mitragynine residue to form a crude mitragynine product including 7-hydroxymitragynine 606. The method includes separating a high-purity 7-hydroxymitragynine product from the crude mitragynine product 607 and collecting the high-purity 7-hydroxymitragynine product 608.

Referring to FIG. 7, a method 700 of synthesizing 7-hydroxymitragynine includes dissolving a predetermined volume of mitragynine extract in a solvent including tetrahydrofuran (THF) and water to form a first mitragynine solution 701. The first mitragynine solution is cooled to a temperature ranging from about-5 degrees Celsius to about 5 degrees Celsius 702. PIFA is added to the first mitragynine solution 703. The first mitragynine solution is allowed to react with the solvent and the PIFA to form a second mitragynine solution 704. The second mitragynine solution is quenched with a saturated sodium bicarbonate solution to form a third mitragynine solution 705. Ethyl acetate is added to the third mitragynine solution to extract a crude mitragynine product including 7-hydroxymitragynine 706. Alkaline column chromatography using an alkaline column is performed on the crude mitragynine product including 7-hydroxymitragynine 707. A high-purity 7-hydroxymitragynine product is collected from the alkaline column 708.

In practice, employing a solvent mixture of tetrahydrofuran and water has been found to provide a balanced medium for the reaction.

Additionally, using low-temperature conditions, as described herein, has been found to minimize by-product formation.

The stepwise extraction and purification processes, as described herein, have been found to maximize yield and purity.

Exemplary Protocol for Synthesizing 7-Hydroxymitragynine:

Preparation:

Mitragynine is dissolved in a mixed solvent of tetrahydrofuran (THF) and water under an argon atmosphere.

As an example, 1 g mitragynine is added per 0.1-2 ml organic solvent or a blend of organic solvents.

The mitragynine may be purged and backfilled with a positive pressure of from 0.1-20 psi.

Reaction:

The solution is cooled to −5° C. to +5° C., and PIFA is added (e.g., 0.1-2 g PIFA to 1 g mitragynine). The mixture is allowed to react for 2-10 hours.

Quenching:

The reaction is quenched with a saturated sodium bicarbonate solution, adjusting the pH to 7-9.5.

Extraction:

The mixture is extracted with ethyl acetate and washed with saturated saline, followed by drying over anhydrous sodium sulfate.

Another organic solvent or organic solvent blend washed with saline 1-6 times and dried via anhydrous sodium sulphate or anhydrous sodium carbonate may be employed.

Purification:

The crude product is subjected to alkaline column chromatography using a silica gel column modified with triethylamine and petroleum ether, eluted with a 1:1 mixture of ethyl acetate and light petroleum.

Preparation of Alkaline Silica Gel Column:

The column is prepared by rinsing common silica gel with triethylamine followed by petroleum ether to achieve the alkaline environment for purification.

An example of the synthesis method includes reacting 18-21 mg of mitragynine with 29-33 mg of PIFA at 0° C. for 3-5 hours in a mixture of 0.9-1.1 mL THF and 0.3-0.6 mL water. The reaction is quenched, extracted, and purified as described herein, yielding a faint yellow solid with a purity of approximately 95% 7-hydroxymitragynine.

In an aspect of the present disclosure, the predetermined volume of mitragynine extract is dissolved in the solvent including THF and water under an argon atmosphere.

In an aspect of the present disclosure, the first mitragynine solution is allowed to react with the solvent and the PIFA for from about 2 hours to about 10 hours.

In an aspect of the present disclosure, quenching the second mitragynine solution includes adjusting the pH of the second mitragynine solution to be from about 7 to about 9.5.

In an aspect of the present disclosure, extracting the crude mitragynine product including 7-hydroxymitragynine includes washing the crude mitragynine product including 7-hydroxymitragynine with saline.

In an aspect of the present disclosure, the washed crude mitragynine product including 7-hydroxymitragynine is dried over anhydrous sodium sulfate.

In an aspect of the present disclosure, the alkaline column is a silica gel column modified with triethylamine and petroleum ether.

In an aspect of the present disclosure, the silica gel column is eluted with a 1:1 mixture of ethyl acetate and petroleum ether.

In an aspect of the present disclosure, the alkaline column has a pH ranging from about 7 to about 11.

In an aspect of the present disclosure, 0.1-2 g of PIFA is added to the first mitragynine solution per 1 g of mitragynine extract.

In an aspect of the present disclosure, the alkaline column is prepared by rinsing silica gel with triethylamine.

Referring to FIG. 8, a method 800 of synthesizing 7-hydroxymitragynine includes dissolving a predetermined volume of mitragynine extract in a solvent to form a first mitragynine solution 801. The method includes cooling the first mitragynine solution to a temperature ranging from about-5 degrees Celsius to about 5 degrees Celsius 802. PIFA is added to the first mitragynine solution 803. The first mitragynine solution is allowed to react with the solvent and the PIFA to form a second mitragynine solution 804. The second mitragynine solution is quenched with a saturated sodium bicarbonate solution to form a third mitragynine solution 805. The method includes adding an organic solvent to the third mitragynine solution to extract a crude mitragynine product including 7-hydroxymitragynine 806. Alkaline column chromatography using an alkaline column is performed on the crude mitragynine product including 7-hydroxymitragynine 807. A high-purity 7-hydroxymitragynine product is collected from the alkaline column 808.

Referring to FIG. 9, a method 900 of synthesizing 7-hydroxymitragynine includes dissolving a predetermined volume of mitragynine extract in a solvent to form a first mitragynine solution 901. PIFA is added to the first mitragynine solution 902. The method includes allowing the first mitragynine solution to react with the solvent and the PIFA to form a second mitragynine solution 903. The second mitragynine solution is quenched with a saturated sodium bicarbonate solution to form a third mitragynine solution 904. An organic solvent is added to the third mitragynine solution to extract a crude mitragynine product including 7-hydroxymitragynine 905. The method includes separating a high-purity 7-hydroxymitragynine product from the crude mitragynine product 906 and collecting the high-purity 7-hydroxymitragynine product 907.

Conventional delivery and enhancement methods for 7-hydroxymitragynine do not sufficiently address the full potential of its therapeutic benefits, often leading to increased dosages with associated risks.

Aspects of the present disclosure provide methods and formulations for enhancing the pharmacological effects of 7-hydroxymitragynine through co-administration with one or more of a number of potentiators. These include agmatine, liposomal vitamin C, tyramines with known modulator affinity, CYP450 inhibitors, NMDA receptor agonists, antidepressants, GABA agonists, muscle relaxants, and antihistamines. This multi-faceted potentiation approach has been found to improve absorption, and synergistically enhance analgesic efficacy.

A method of administering a therapeutic formulation including administering a compound having the structure:

in which R2 is —H or -alkyl, R3 is —H or -alkyl, and R4 is —H or -alkyl. The method includes administering a potentiator of the compound. The potentiator is configured to enhance analgesic efficacy of the compound.

In an aspect of the present disclosure, the potentiator is agmatine.

In an aspect of the present disclosure, the potentiator is liposomal vitamin C.

In an aspect of the present disclosure, the potentiator is a tyramine.

In an aspect of the present disclosure, the potentiator is octopamine, dopamine, or norepinephrine.

In an aspect of the present disclosure, the potentiator is a CYP450 inhibitor.

In an aspect of the present disclosure, the CYP450 inhibitor is grapefruit juice, ketoconazole, or erythromycin.

In an aspect of the present disclosure, the potentiator is an NMDA receptor agonist.

In an aspect of the present disclosure, the potentiator is an antidepressant.

In an aspect of the present disclosure, the potentiator is a GABA agonist.

In an aspect of the present disclosure, the potentiator is a muscle relaxant.

In an aspect of the present disclosure, the potentiator is an antihistamine.

Provided in accordance with aspects of the present disclosure is a therapeutic formulation including a compound having the structure:

in which R2 is —H or -alkyl, R3 is —H or -alkyl, and R4 is —H or -alkyl. The therapeutic formulation includes a potentiator of the compound. The potentiator is configured to enhance analgesic efficacy of the compound.

In an aspect of the present disclosure, the potentiator of the therapeutic formulation is agmatine.

In an aspect of the present disclosure, the potentiator of the therapeutic formulation is liposomal vitamin C.

In an aspect of the present disclosure, the potentiator of the therapeutic formulation is a tyramine.

In an aspect of the present disclosure, the potentiator of the therapeutic formulation is octopamine, dopamine, or norepinephrine.

In an aspect of the present disclosure, the potentiator of the therapeutic formulation is a CYP450 inhibitor.

In an aspect of the present disclosure, the potentiator of the therapeutic formulation is grapefruit juice, ketoconazole, or erythromycin.

In an aspect of the present disclosure, the potentiator of the therapeutic formulation is the potentiator is an NMDA receptor agonist.

In an aspect of the present disclosure, the potentiator of the therapeutic formulation is an antidepressant.

In an aspect of the present disclosure, the potentiator of the therapeutic formulation is a GABA agonist.

In an aspect of the present disclosure, the potentiator of the therapeutic formulation is a muscle relaxant.

In an aspect of the present disclosure, the potentiator of the therapeutic formulation is an antihistamine.

Provided in accordance with aspects of the present disclosure is a carrier for administering a therapeutic formulation including a compound having the structure:

in which R2 is —H or -alkyl, R3 is —H or -alkyl, and R4 is —H or -alkyl. The carrier includes a potentiator of the compound. The potentiator is configured to enhance analgesic efficacy of the compound. The carrier is configured to administer the compound and the potentiator to a user.

In an aspect of the present disclosure, the potentiator of compound included in the carrier is agmatine, liposomal vitamin C, a tyramine, octopamine, dopamine, norepinephrine, a CYP450 inhibitor, grapefruit juice, ketoconazole, or erythromycin, an NMDA receptor agonist, an antidepressant, a GABA agonist, a muscle relaxant, or an antihistamine.

In an aspect of the present disclosure, the carrier is configured to administer the compound and the potentiator to the user by oral delivery, transdermal delivery, parenteral delivery, pulmonary delivery, inhalation delivery, intramuscular delivery, subcutaneous delivery, rectal delivery, or topical delivery.

As an example, parenteral formulations may range from half a milligram to 5000 mg (e.g., of a high purity 7-hydroxymitragynine product, as described herein).

In an aspect of the present disclosure, the carrier is a transdermal patch.

In an aspect of the present disclosure, the transdermal patch is a slow release patch, a reservoir patch, a matrix patch, a drug-in-adhesive patch, a vapor patch, a microneedle patch, a reservoir-in-matrix patch, or an active transdermal patch.

As an example, transdermal formulations range from half a milligram to 5000 mg (e.g., of a high purity 7-hydroxymitragynine product, as described herein). Transdermal formulations may include instant release or sustained release formulations.

Exemplary Protocol for Administering a Transdermal Patch:

Administering a transdermal patch containing 7-hydroxymitragynine. An exemplary patch is designed to deliver 2 milligrams (e.g., of a high purity 7-hydroxymitragynine product, as described herein) per hour over a 24-hour period:

Pre-Administration Assessment:

Patient Assessment:

Evaluate the patient's medical history, current medications, and any potential allergies, particularly to adhesive materials or opioids.

Indication Confirmation:

Ensure that the use of a 7-hydroxymitragynine patch is indicated for the patient's condition and that alternative treatments have been considered.

Skin Examination:

Inspect the skin where the patch will be applied, ensuring it is clean, dry, and free of cuts, rashes, or irritations.

Preparation:

Hand Hygiene:

Wash hands thoroughly with soap and water before handling the transdermal patch.

Patch Preparation:

Remove the patch from its sealed package without touching the sticky adhesive part. If necessary, cut the patch to the prescribed size before removing the liner, using clean scissors.

Patch Application:

Site Selection:

Choose an area on the upper body or upper outer part of the arm. Avoid areas with excessive hair, skin folds, or high movement. Alternate the application site with each new patch to prevent skin irritation.

Skin Prep:

Clean the selected area with soap and water, drying completely. Avoid using alcohol or other solvents that might irritate the skin.

Application:

Remove the protective liner from the patch. Apply the patch firmly with the adhesive side down, pressing firmly for about 30 seconds to ensure good contact, especially around the edges.

During Use:

Monitoring:

Check the patch periodically to ensure it remains adhered to the skin. If the patch becomes loose, secure the edges with medical tape.

Side Effects Monitoring:

Monitor the patient for signs of side effects.

Documentation:

Keep detailed records of patch applications, changes, and any observations about efficacy and side effects.

Patch Removal and Disposal:

Removal: After 24 hours, or as directed by a healthcare provider, carefully peel the patch off. Fold the patch in half with the adhesive side inward and press together.

Skin Care Post-Removal:

Clean the area with soap and water to remove any adhesive residue. Inspect the skin for any signs of irritation or adverse reaction.

Disposal:

Dispose of the used patch by folding it in half with the sticky sides together and placing it in a closed trash container away from children and pets. Do not flush the patch down the toilet.

Patient Education:

Instructions for Use: Educate the patient on how to apply and remove the patch, the importance of rotating the application site, and the need to keep the patch dry.

Inform the patient about possible side effects, such as extreme drowsiness.

Follow-Up: Arrange for follow-up visits to monitor the patient's response to treatment and adjust the treatment plan, as necessary.

Exemplary Arrangement of a Transdermal Patch

Patch ingredients may include:

Polymer matrix: This is the base material of the patch gel that holds the medication and facilitates its release through the skin. Common polymers used include acrylic polymers, silicones, and ethylene vinyl acetate (EVA).

Solvents: Solvents are used to dissolve the medication and aid in its dispersion within the polymer matrix. Common solvents include water, ethanol, propylene glycol, and glycerin.

Medication: The active ingredient(s) of the patch gel would include 2 mg/24 hours 7-hydroxymitragynine (e.g., of a high purity 7-hydroxymitragynine product, as described herein) but could include a range of strengths depending on the application.

Penetration enhancers: Some formulations may include penetration enhancers to help the medication penetrate the skin more effectively. Common penetration enhancers include fatty acids, alcohols, and surfactants.

Stabilizers and preservatives: These ingredients help maintain the stability of the gel formulation and prevent degradation of the medication over time. Stabilizers may include antioxidants, while preservatives are used to prevent microbial growth.

Adhesive: An adhesive layer is often included to ensure that the patch adheres firmly to the skin during wear. The adhesive may be made from synthetic polymers or natural materials like acrylate copolymers.

Backing layer: This is typically a protective layer that covers the adhesive side of the patch until it is ready for use. It is often made from materials like polyester or polyethylene.

Liner: Some patches include a liner that is removed before application to expose the adhesive layer. The liner is typically made from materials like silicone-coated paper or film.

In an aspect of the present disclosure, the carrier is an inhaler or a vaporizer.

In an aspect of the present disclosure, the carrier includes a cartridge configured to hold the compound and the potentiator of the compound. The cartridge is configured to be operably coupled with the inhaler or the vaporizer.

As an example, vaporization of 7-hydroxymitragynine (e.g., of a high purity 7-hydroxymitragynine product, as described herein) may be achieved within hardware that has a heating element and controlled temperature output for precise delivery of the active compound through vapors with dosages of a microgram (e.g., 250 mg per dose).

Vaporization of this compound (e.g., of a high purity 7-hydroxymitragynine product, as described herein) may be used for anesthesia, pain relief, or substance use disorders.

The optimal vaporization temperature of 7-hydroxymitragynine is from about 200 degrees Celsius to about 600 degrees Celsius. It has been found that highly effective vaporization is achieved at from about 350 degrees Celsius to about 600 degrees Celsius. Vapor device heating elements could be other material than ceramic as well such as titanium, carbon composite.

Cartridge Components:

a Digitally Controlled Battery:

This may be employed as the core power source of a cartridge system, typically made up of a rechargeable lithium-ion battery. The "digitally controlled" aspect refers to the system's ability to adjust and control the temperature and power output through electronic controls, often with a microcontroller. This allows the manufacturer to customize the vaping experience based on performance necessities and ensures consistent performance. The battery may feature a small digital display or LED indicators that show settings such as temperature and battery life.

Ceramic Heating Element:

This element may be employed for heating 7-hydroxymitragynine without burning it, which allows for the extraction of active ingredients without producing harmful byproducts typical of combustion. Ceramic is favored for its neutral impact on flavor, as well as its ability to provide a consistent heat distribution. This reduces the risk of hot spots and provides a more efficient vaporization process.

Removable Pod:

This component is a small, replaceable, and optionally refillable container that holds the material to be vaporized. Pods are designed to be easy to insert and remove from the main device, offering convenience and flexibility. They typically connect to the heating element and can be swapped out quickly for different flavors or materials, or replaced when they wear out. Some pods are designed with integrated coils and wicks that absorb the material and bring it into contact with the heating element, while others may use a wickless design where the material is in direct contact with the ceramic.

The manufacturer programs the desired temperature via the controls on a microcontroller connected to the battery. The battery then powers the ceramic heating element, which heats the material within the pod to the set temperature. Temperature, optical vapor characteristics, voltage, resistance and amperage are monitored by the microcontroller to provide the optimal output from the battery.

Exemplary Protocol for Administering 7-hydroxymitragynine by an Inhaler or Vaporizer:

Administering 7-hydroxymitragynine through an inhaler or vaporizer involves precise dosage and patient education to ensure effective and safe use. Below is a detailed protocol for the administration of an inhaler or vaporizer designed to deliver 0.1 milligrams (e.g., of a high purity 7-hydroxymitragynine product, as described herein) per inhalation:

Pre-Administration Assessment:

Patient Assessment:

Evaluate the patient's medical history, such as respiratory issues, current medications, potential allergies, and any previous experiences with inhalation therapy.

Indication Confirmation:

Confirm that inhalation is an appropriate delivery method for the patient's condition and that the use of 7-hydroxymitragynine is indicated.

Device Inspection:

Ensure that the inhaler or vaporizer is clean, functioning correctly, and correctly calibrated to deliver the prescribed dose.

Preparation:

Hand Hygiene:

Wash hands thoroughly with soap and water to prevent contamination of the device.

Device Preparation:

If using a new device or cartridge, follow the manufacturer's instructions to prepare it for use. This might include priming the device to ensure proper aerosolization of the medication.

Administration Procedure:

Instructions for Use:

Positioning:

Educate the patient to sit or stand upright for optimal inhalation.

Breathing Technique:

Instruct the patient to exhale fully to empty the lungs before using the inhaler.

Device Activation:

Teach the patient to activate the inhaler or vaporizer while starting a slow and deep inhalation through the mouth.

Inhalation and Hold:

Advise the patient to hold their breath for 5-10 seconds after inhaling the dose to allow the medication to settle in the lungs.

Repetition:

Depending on the prescribed dosage, instruct the patient on how many inhalations are needed and the interval between them.

Dosage Monitoring:

Ensure the patient understands how to track doses, especially if the device does not have a dose counter.

During Use:

Monitoring for Effectiveness:

Effectiveness:

Ask the patient to report the relief of symptoms or any unexpected outcomes.

Adverse Reactions: Monitor for and educate about possible side effects such as cough, throat irritation, or systemic effects like nausea or dizziness.

Device Maintenance:

Cleaning and Storage: Instruct the patient on how to clean and store the device according to the manufacturer's guidelines to maintain device function and hygiene.

Regular Inspection:

Encourage regular checks of the device for any signs of wear or malfunction.

Patient Education:

Proper Technique:

Reinforce training on the correct use of the inhaler or vaporizer.

Symptom Monitoring:

Educate the patient to monitor their symptoms and the effectiveness of the treatment.

Follow-Up:

Schedule follow-up appointments to reassess the patient's condition, the effectiveness of the therapy, and to make any necessary adjustments to the treatment plan.

In an aspect of the present disclosure, the carrier is a tablet, a tincture, a suspension, or an emulsion.

As an example, a tablet may include a dosage of 0.5 mg to 250 mg mitragynine (e.g., of a high purity 7-hydroxymitragynine product, as described herein) combined with one or more of the potentiators described herein.

To prepare a tablet, one or more alkaloids of mitragynine (e.g., including exclusively or in part the high purity 7-hydroxymitragynine product, as described herein) may be homogenously mixed into inert binders, fillers, and lubricant powders, and fed into a hopper of a rotary tablet press.

Tablet formulations may be configured to be instant release, enteric coding, sustained release, sublingual, and/or dissolvable.

In an aspect of the present disclosure, the carrier includes lactose, sucrose, gelatine, or agar.

In an aspect of the present disclosure, the carrier includes saline, or a dextrose solution.

In an aspect of the present disclosure, the carrier includes a binder, a lubricant, a dilutant, a disintegrating agent, a coloring agent, a flavoring agent, or a preservative.

Various mitragynine alkaloids, which can act as opioid receptor modulators, are described in the following patents and patent application publications, the entire contents of each of which are incorporated by reference herein in their entireties. CN106967067A filed on May 25, 2017, and published on Jul. 21, 2017. WO2016176657A1 filed on Apr. 29, 2016, and published on Nov. 3, 2016. WO2017165738A, filed on Mar. 24, 2017, and published on Sep. 28, 2017. U.S. Pat. No. 10,961,244B2 filed on Sep. 25, 2018, and issued on Mar. 30, 2021. U.S. Pat. No. 11,912,707B2 filed on Mar. 2, 2021, and issued on Feb. 27, 2024.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A method of converting mitragynine to 7-hydroxymitragynine, comprising:

dissolving a predetermined volume of mitragynine extract in a solvent to form a first mitragynine solution in a first vessel;

adjusting the temperature of the first vessel to about 0 degrees Celsius;

adding a second solution including sodium bicarbonate and water and a third solution including oxone monopersulfate and water to the first vessel including the first mitragynine solution;

allowing the first mitragynine solution to react with the second solution including sodium bicarbonate and water and the third solution including oxone monopersulfate and water to form a second mitragynine solution;

passing the second mitragynine solution through a filtration apparatus including at least one filtration membrane to form a third mitragynine solution captured in a second vessel;

transferring the third mitragynine solution to an evaporator apparatus;

removing at least 60% of the solvent from the third mitragynine solution to form a fourth mitragynine solution by evaporating the solvent from the third mitragynine solution;

transferring the fourth mitragynine solution to a third vessel;

mixing pure ethyl acetate with the fourth mitragynine solution to form a fifth mitragynine solution;

spinning the fifth mitragynine solution to form an aqueous layer and an ethyl acetate extract enriched with 7-hydroxymitragynine;

performing phase separation chromatography using a phase separation column including at least one organic solvent on the ethyl acetate extract enriched with 7-hydroxymitragynine; and collecting a high-purity 7-hydroxymitragynine product from the phase separation column.

2. The method of claim 1, wherein the first vessel is maintained at the temperature of about 0 degrees Celsius in a reactor including a chiller configured to maintain a temperature of the first vessel.

3. The method of claim 2, wherein the reactor includes a stirrer, and wherein the second solution including sodium bicarbonate and water and the third solution including oxone monopersulfate and water are added to the first vessel substantially simultaneously while being continuously stirred by the stirrer of the reactor.

4. The method of claim 3, wherein the reaction between the first mitragynine solution and the second solution including sodium bicarbonate and water and the third solution including oxone monopersulfate and water is allowed to proceed for 60 minutes while a reaction chamber of the reactor is maintained with an argon atmosphere, and wherein the first vessel is maintained at about 0 degrees Celsius for the duration of the 60 minutes by the reactor.

5. The method of claim 1, wherein the at least one filtration membrane of the filtration apparatus includes a micron scale separation screen and at least one layer of filter paper secured by an O-ring.

6. The method of claim 1, wherein forming the fourth mitragynine solution includes removing at least 99% of the solvent by volume from the third mitragynine solution by evaporating the solvent from the third mitragynine solution.

7. The method of claim 1, wherein the sodium bicarbonate solution is prepared by stirring sodium bicarbonate into water in a first preparation vessel, and wherein the oxone monopersulfate solution is separately prepared by stirring oxone monopersulfate into water in a second preparation vessel.

8. The method of claim 1, wherein forming the fourth mitragynine solution includes removing at least 99% of the solvent by volume from the third mitragynine solution by evaporating the solvent from the third mitragynine solution, and wherein the evaporating is performed using a rotary evaporator set at about 50 degrees Celsius and about 60 revolutions per minute (RPM) under vacuum conditions.

9. The method of claim 1, wherein the fifth mitragynine solution is spun at least once at about 200 RPM and then allowed to settle for about 3 minutes.

10. The method of claim 1, wherein the at least one organic solvent includes a blend of organic solvents each dissolved in a ratio of about 0.5 to about 10 ml organic solvent to 1 gram mitragynine, and wherein residual organic solvents of the blend of organic solvents are removed from the phase separation column under vacuum conditions to yield the high-purity 7-hydroxymitragynine product from the phase separation column.

11. The method of claim 1, wherein the at least one organic solvent is removed from the phase separation column by a vacuum oven maintained at from 25 degrees Celsius to 75 degrees Celsius.

12. The method of claim 1, wherein the high-purity 7-hydroxymitragynine product contains at least 95% 7-hydroxymitragynine and no more than 5% mitragynine.

13. A method of converting mitragynine to 7-hydroxymitragynine, comprising:

dissolving a predetermined volume of mitragynine extract in a solvent to form a first mitragynine solution in a first vessel;

adding a second solution including sodium bicarbonate and water and a third solution including oxone monopersulfate and water to the first vessel including the first mitragynine solution;

allowing the first mitragynine solution to react with the second solution including sodium bicarbonate and water and the third solution including oxone monopersulfate and water to form a second mitragynine solution;

passing the second mitragynine solution through a filtration apparatus including at least one filtration membrane to form a third mitragynine solution captured in a second vessel;

mixing pure ethyl acetate with the third mitragynine solution to form a fourth mitragynine solution, wherein the fourth mitragynine solution contains no so solvents other than ethyl acetate;

spinning the fourth mitragynine solution to form an aqueous layer and an ethyl acetate extract enriched with 7-hydroxymitragynine;

performing phase separation chromatography using a phase separation column including at least one organic solvent on the ethyl acetate extract enriched with 7-hydroxymitragynine; and collecting a high-purity 7-hydroxymitragynine product from the phase separation column.

* * * * *